US008434166B2

(12) United States Patent
Friton

(10) Patent No.: US 8,434,166 B2
(45) Date of Patent: May 7, 2013

(54) ARTICLE OF HEADWEAR WITH PERIPHERAL SUPPORT

(75) Inventor: Michael R. Friton, Portland, OR (US)

(73) Assignee: Nike, Inc., Beaverton, OR (US)

(*) Notice: Subject to any disclaimer, the term of this patent is extended or adjusted under 35 U.S.C. 154(b) by 636 days.

(21) Appl. No.: 10/985,034

(22) Filed: Nov. 10, 2004

(65) Prior Publication Data

US 2006/0096004 A1    May 11, 2006

(51) Int. Cl.
*A42B 1/00* (2006.01)
(52) U.S. Cl.
USPC ........................................ 2/209.11; 2/171.03
(58) Field of Classification Search ............... 2/209.11, 2/171.03, 172, 171.6, 181.8, 120, 425, 10, 2/12, 195.7, 175.1, 175.2, 175.3, 175.4, 175.5, 2/175.6, 195.5, 195.6, 468
See application file for complete search history.

(56) References Cited

U.S. PATENT DOCUMENTS

| | | | | |
|---|---|---|---|---|
| 2,149,468 A | * | 3/1939 | Santise | 2/175.5 |
| 2,663,024 A | * | 12/1953 | Cantor | 2/175.5 |
| 2,684,483 A | | 7/1954 | Kwake | |
| 2,845,289 A | * | 7/1958 | Cicogna | 2/257 |
| 3,314,077 A | * | 4/1967 | Marchello | 2/421 |
| 4,096,590 A | * | 6/1978 | Keshock | 2/175.5 |
| 4,815,148 A | | 3/1989 | Satterfield | |
| 4,999,851 A | * | 3/1991 | Hall | 2/175.5 |
| 5,031,246 A | | 7/1991 | Kronenberger | |
| 5,272,772 A | | 12/1993 | Hahn | |
| 5,323,491 A | * | 6/1994 | Barrett, Jr. | 2/207 |
| 5,367,706 A | | 11/1994 | Davidson | |
| 5,615,415 A | | 4/1997 | Beckerman | |
| 5,664,257 A | | 9/1997 | Hall | |
| 5,664,261 A | | 9/1997 | Lacy | |
| 5,715,540 A | | 2/1998 | Cho | |
| 5,799,335 A | | 9/1998 | Ethler | |
| 5,845,339 A | * | 12/1998 | Ashley et al. | 2/195.6 |
| 5,857,219 A | * | 1/1999 | Edmark | 2/182.2 |
| 5,950,241 A | * | 9/1999 | Gomez | 2/172 |
| 6,122,774 A | | 9/2000 | Park | |
| 6,216,277 B1 | * | 4/2001 | Cheng | 2/171.03 |
| 6,256,794 B1 | * | 7/2001 | Erickson | 2/209.11 |
| 6,260,204 B1 | * | 7/2001 | Morrissey | 2/172 |
| 6,260,208 B1 | * | 7/2001 | Wang | 2/209.11 |
| 6,421,886 B1 | * | 7/2002 | Oetiker | 24/23 R |
| 6,526,586 B2 | * | 3/2003 | Gattamorta | 2/12 |
| 6,561,393 B1 | * | 5/2003 | Cheng | 2/171.03 |

* cited by examiner

*Primary Examiner* — Khoa Huynh
*Assistant Examiner* — Sally Haden
(74) *Attorney, Agent, or Firm* — Banner & Witcoff, Ltd.

(57) ABSTRACT

An article of headwear is disclosed that includes a support and a material element secured to the support. The support extends around a periphery of the headwear and has an elongate structure that defines a first end portion and a second end portion. The support is flexed such that the first end portion overlaps the second end portion to define a loop with an interior area, and the end portions may have mating undulating configurations. The material element is secured to the support and extends around the interior area of the loop to define an aperture for receiving a head of an individual. The support may be flexed to form multiple loops and place the headwear in a collapsed configuration.

21 Claims, 9 Drawing Sheets

ARTICLE OF HEADWEAR WITH PERIPHERAL SUPPORT

BACKGROUND OF THE INVENTION

1. Field of the Invention

The present invention relates to headwear. The invention concerns, more particularly, an article of headwear having a peripheral support structure.

2. Description of Background Art

Conventional articles of headwear vary significantly in style and structure to include hats, caps, and visors, for example. In general, the primary elements of the conventional articles of headwear include a crown and a brim. The crown is configured to extend over or around at least a portion of the head of an individual, and the brim extends in an outward direction from a forward region of the crown to provide the face and eyes with protection from light and precipitation, for example. A wide range of materials, natural or synthetic, may be used to form the conventional articles of headwear.

Some articles of headwear may be classified as either fitted headwear or adjustable headwear. Fitted headwear is generally manufactured in a wide range of sizes based upon a circumference of the head, with each size having fixed dimensions to accommodate an individual with corresponding head dimensions. Adjustable headwear, however, incorporates an adjustment system that permits a single article of headwear to accommodate individuals with various head dimensions. Accordingly, adjustable headwear may be manufactured with significantly fewer sizes than fitted headwear to accommodate size ranges rather than a particular size. Although adjustable headwear is generally more complex to manufacture than fitted headwear, the manufacturing efficiency of producing relatively few sizes reduces the overall cost of adjustable headwear in comparison with fitted headwear. Another drawback to adjustable headwear relates to comfort. More particularly, the adjustment system or other portions of the adjustable headwear may form pressure points that decrease the overall comfort of the adjustable headwear.

An article of headwear having the configuration of a baseball cap and incorporating a conventional style of adjustment system is disclosed in U.S. Pat. No. 5,272,772 to Hahn. A rear portion of the baseball cap includes a cut-out area having two overlapping straps that extend from opposite sides of the cut-out area. One of the straps includes a plurality of protrusions and the other strap includes a plurality of corresponding apertures. By varying the protrusions that are received by specific apertures, the circumference of the baseball cap is adjusted. A similar adjustment system is disclosed in U.S. Pat. No. 4,815,148 to Satterfield and incorporates portions of a hook and loop fastener that are located on opposite sides of a slit in a baseball cap.

A drawback to the articles of headwear disclosed in Hahn and Satterfield relates to the aesthetic appearance of the adjustment system. The material forming the crown of fitted headwear generally extends entirely around the head. In contrast, the material forming the crown of the baseball caps of Hahn and Satterfield includes the cut-out area and slit, respectively, which interrupt the continuity of the crown. Accordingly, manufacturers often incorporate an adjustment system into adjustable headwear that provides the appearance of a fitted headwear. For example, U.S. Pat. No. 6,122,774 to Park; U.S. Pat. No. 5,715,540 to Cho; and U.S. Pat. No. 5,615,415 to Beckerman each disclose adjustable headwear that incorporates a stretchable material. U.S. Pat. No. 5,031,246 to Kronenberger discloses adjustable headwear that incorporates an inflatable bladder located within material that forms the bottom of the crown to vary the effective diameter of a headband in the crown.

SUMMARY OF THE INVENTION

The present invention is an article of headwear having a support and a material element secured to the support. The support extends around a periphery of the headwear and has an elongate structure that defines a first end portion and a second end portion. The support is flexed such that the first end portion overlaps the second end portion to define a loop with an interior area, and the end portions may have mating undulating configurations. The material element is secured to the support and extends around the interior area of the loop to define an aperture for receiving a head of an individual. The support may be flexed to form multiple loops and place the headwear in a collapsed configuration.

The material element may have a c-shaped configuration with a central area and two end areas, the end areas being joined to form the aperture. In some embodiments, the material element is formed of unitary construction from elastic textiles, and an edge of the first material element wraps around the support to define a tubular structure for receiving the support.

The headwear may also include another material element located substantially within the interior area of the loop and extending only partially around the interior area of the loop. This material element may have a crescent-shaped configuration and may be positioned adjacent the first end portion and the second end portion of the support.

The advantages and features of novelty characterizing the present invention are pointed out with particularity in the appended claims. To gain an improved understanding of the advantages and features of novelty, however, reference may be made to the following descriptive matter and accompanying drawings that describe and illustrate various embodiments and concepts related to the invention.

DESCRIPTION OF THE DRAWINGS

The foregoing Summary of the Invention, as well as the following Detailed Description of the Invention, will be better understood when read in conjunction with the accompanying drawings.

DETAILED DESCRIPTION OF THE INVENTION

The following discussion and accompanying figures disclose an article of headwear 10 in accordance with the present invention. Headwear 10 is disclosed as having the configuration of a visor. Concepts related to the present invention, however, may be applied to a variety of headwear styles, in addition to the visor. Accordingly, caps, hats, and other types of headwear may also incorporate the concepts disclosed in relation to headwear 10.

Figure 1:
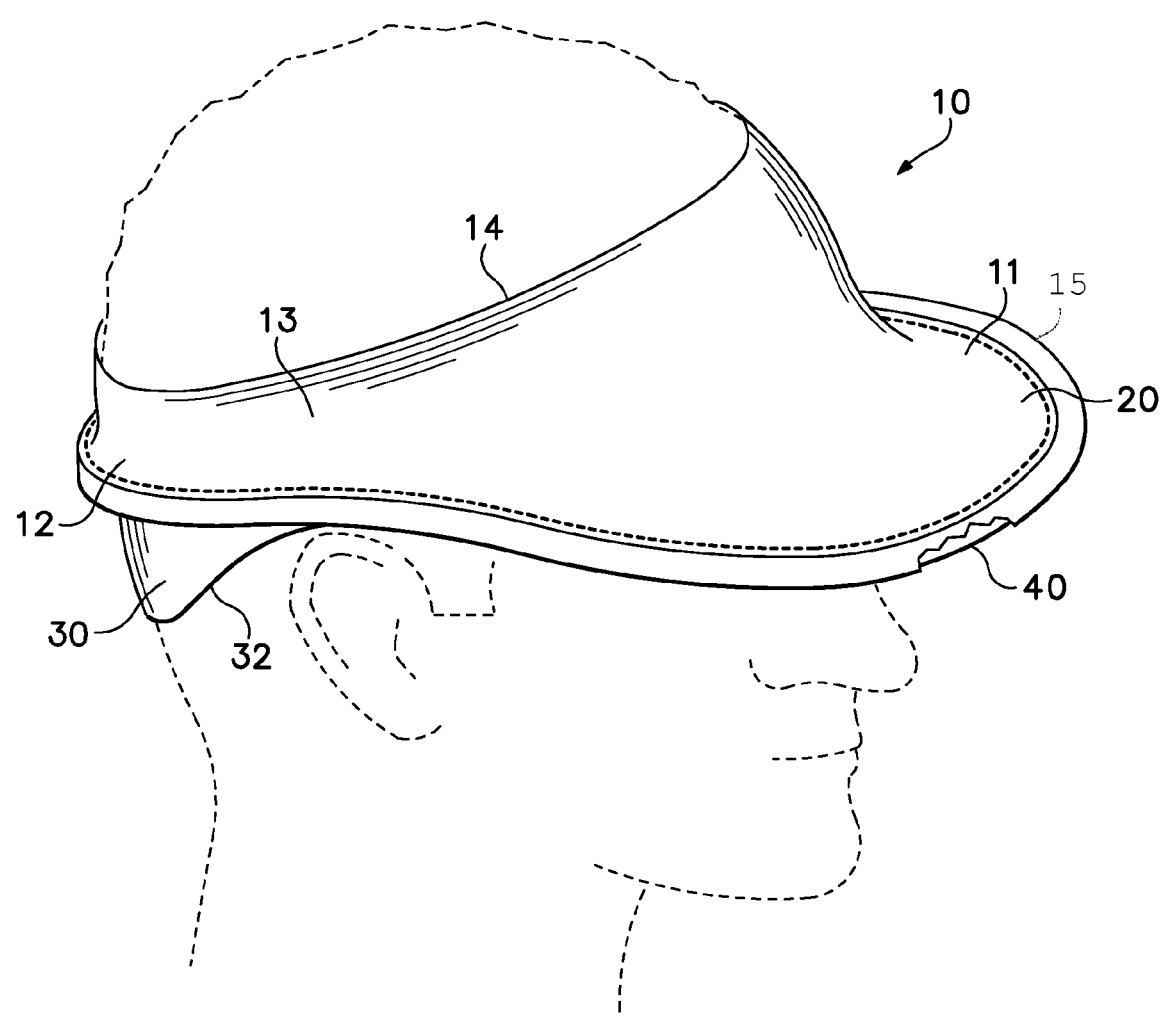
FIG. 1 is a perspective view of an article of headwear.
Figure 2:
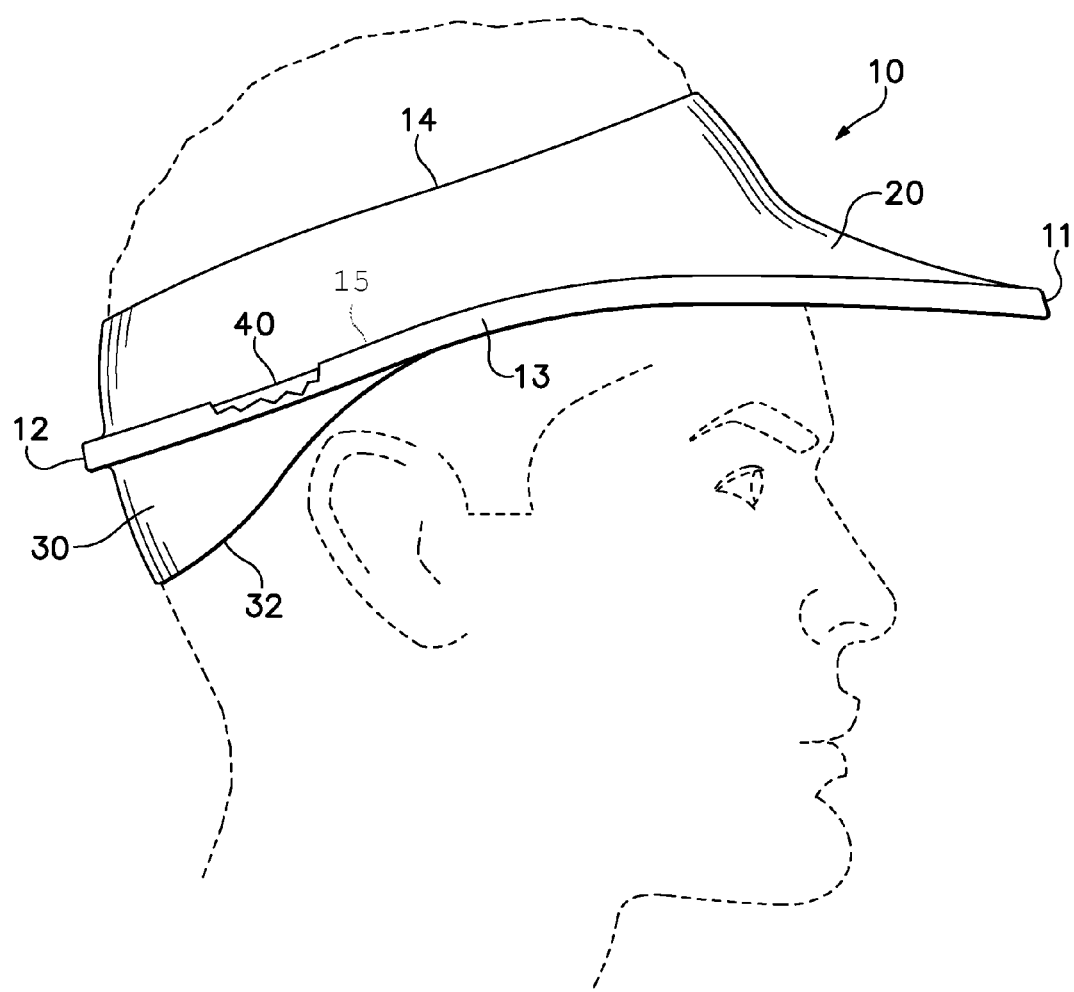
FIG. 2 is a side elevational view of the article of headwear.

Headwear 10 forms a forward region 11, a rearward region 12, and a pair of side regions 13 that extend around an aperture 14. The manner in which headwear 10 is worn by an individual may depend upon various factors that include fashion or stylistic considerations, the personal preferences of the individual, and the intended purpose for wearing headwear 10. A relatively conventional manner of wearing headwear 10, however, is depicted in FIGS. 1 and 2 and involves positioning headwear 10 on a head of the individual such that (a) aperture 14 extends around a circumference of the head, (b) forward region 11 extends outward in a generally horizontal direction to extend over the face of the individual, (c) rearward region 12 extends around a rear area of the head, and (d) side regions 13 are positioned above and adjacent the ears of the individual.

Forward region 11 is positioned above eyes of the individual and forms a brim that blocks light and precipitation from the eyes and face of the individual when headwear 10 is worn in the relatively conventional manner discussed above. Headwear 10 may also be worn in a relatively non-conventional manner. For example, headwear 10 may be positioned on the head such that forward region 11 extends outward from the rear area of the head, and rearward region 12 covers the forehead of the individual. In addition, headwear 10 may be positioned on the head such that forward region 11 extends outward from a side area of the head, or headwear 10 may be worn in an upside-down configuration. Accordingly, terms such as forward, rearward, and side are intended to provide a frame of reference for portions of headwear 10, and are not intended to limit the scope of the present invention or the manner in which headwear 10 may be worn by the individual.

Headwear 10 is formed from three primary components: a first material element 20, a second material element 30, and a support 40. First material element 20 extends through each of regions 11-13 and defines aperture 14. More particularly, first material element 20 is secured to support 40 and extends entirely around the interior area of support 40 to define aperture 14 and block light and precipitation. Second material element 30 is primarily positioned in rearward region 12 and may extend into side regions 13 to form a flap that assists in securing headwear 10 to the head when worn. Support 40 extends around the periphery of headwear 10 and forms a flexible and resilient structure that provides support for material elements 20 and 30 and imparts an overall shape to headwear 10.

Figure 5:
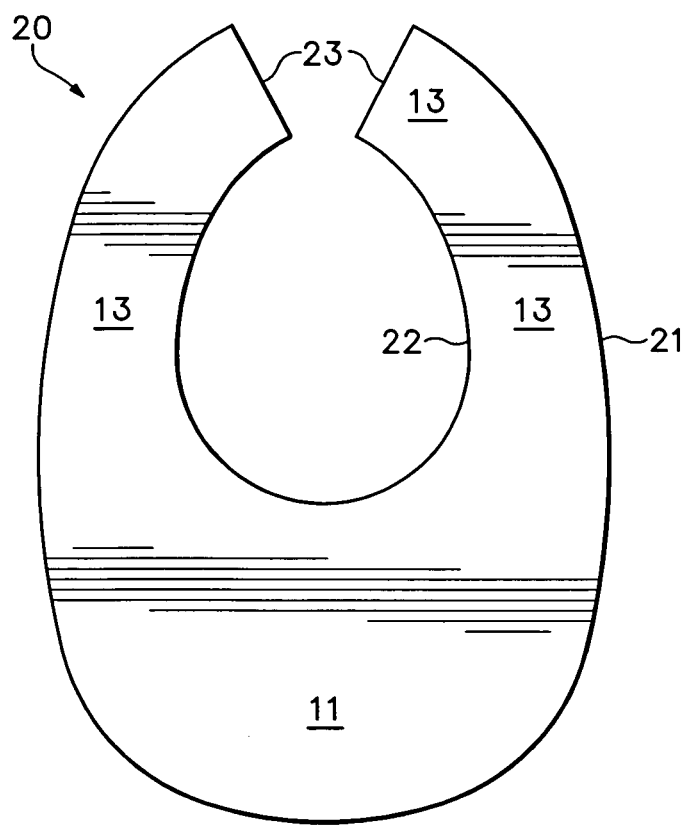
FIG. 5 is a top plan view of a first material element of the article of headwear.

First material element 20 forms a majority of a visible portion of headwear 10. In this regard, first material element 20 extends entirely around an interior area of support 40, thereby extending through each of regions 11-13 and forming aperture 14. With reference to FIG. 5, first material element 20 is depicted individually and defines an outer edge 21, an inner edge 22, and a pair of connecting edges 23. Outer edge 21 and inner edge 22 are generally parallel to each other, and connecting edges 23 extends between end portions of edges 21 and 22.

When incorporated into headwear 10, first material element 20 wraps around support 40 and a line of stitching 21a runs adjacent to outer edge 21 in order to secure to first material element 20 to support 40. Outer edge 21 is, therefore, folded around support 40 to form a generally tubular structure that receives support 40. Inner edge 22 is spaced inward from support 40 and is primarily responsible for forming aperture 14. Connecting edges 23 overlap each other in rearward region 12, or may alternately be placed in an abutting relationship with each other, and are joined together with at least one line of stitching 23a.

First material element 20 is formed from a flexible and generally two-dimensional material. As utilized with respect to the present invention, the term "two-dimensional material" is intended to encompass generally flat materials exhibiting a length and a width that are substantially greater than a thickness. Accordingly, suitable materials for first material element 20 includes various textiles and polymer sheets, for example. The polymer sheets may be extruded, rolled, or otherwise formed from a polymer material to exhibit a generally flat aspect. The textiles are generally manufactured from fibers, filaments, or yarns that are, for example, either (a) produced directly from webs of fibers by bonding, fusing, or interlocking to construct non-woven fabrics and felts or (b) formed through a mechanical manipulation of yarn to produce a woven or knitted fabric. The textiles may incorporate fibers that are arranged to impart one-directional stretch or multi-directional stretch. An example of a suitable textile is a weft knitting spacer mesh formed from approximately 56 percent polyester, 26 percent mono polyester, and 18 percent elastane fibers, which is available from the Gold Long John International Company of Taiwan. In addition to textiles and polymer sheets, other two-dimensional materials may form first material element 20.

Second material element 30 is positioned in rearward region 12 such that end areas of second material element 30 extend into each of side regions 13. Whereas first material element 20 extends entirely around the interior area of support 40, second material element 30 extends only partially around the interior area of support 40. In some embodiments, second material element 30 may extend through a greater portion of the interior area of support 40, second material element 30 may extend entirely around the interior area of support 40, or second material element 30 may be limited to rearward region 12. Any of the materials discussed above for first material element 20 may be utilized for second material element 30.

Figure 6:
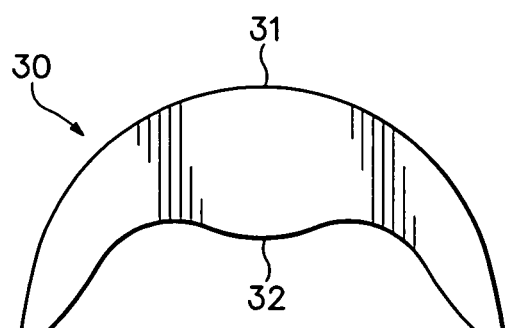
FIG. 6 is a top plan view of a second material element of the article of headwear.

With reference to FIG. 6, second material element 30 is depicted as exhibiting a generally crescent-shaped configuration that defines an outer edge 31 and an inner edge 32. When incorporated into headwear 10, second material element 30 forms a flap that generally enhances the fit of headwear 10 and assists in securing headwear 10 to the head of the individual, as depicted in FIGS. 1 and 2. In contrast with first material element 20, which extends in a generally upward direction when worn, second material element 30 extends in a generally downward direction. When headwear 10 is worn such that rearward region 12 covers the forehead of the individual, for example, second material element 30 may form a sweatband that wicks moisture away from the head. Outer edge 31 is depicted as having a generally semi-circular or otherwise rounded shape that corresponds with the curvature in support 40. In contrast, inner edge 32 has an undulating configuration. In further embodiments, inner edge 32 may exhibit a non-undulating configuration.

As discussed above, first material element 20 wraps around support 40 and stitching 21a runs adjacent to outer edge 21 in order to secure to first material element 20 to support 40. Accordingly, stitching 21a joins outer edge 21 to a more central portion of first material element 20 in order to form the generally tubular structure 15 that receives support 40. In order to incorporate second material element 30 into headwear 10, second material element 30 may be joined to first material element 20 with stitching 21a. More particularly, outer edge 31 may extend between outer edge 21 and the more central portion of first material element 20 such that stitching 21a extends through each of first material element 20 and second material element 30. In further embodiments of the invention, second material element 30 may be joined with separate stitching, thermal bonding, or an adhesive, for example. Accordingly, a variety of method may be utilized to incorporate second material element 30 into headwear 10. In yet further embodiments of the invention, second material element 30 may be absent from headwear 10.

Figure 7:
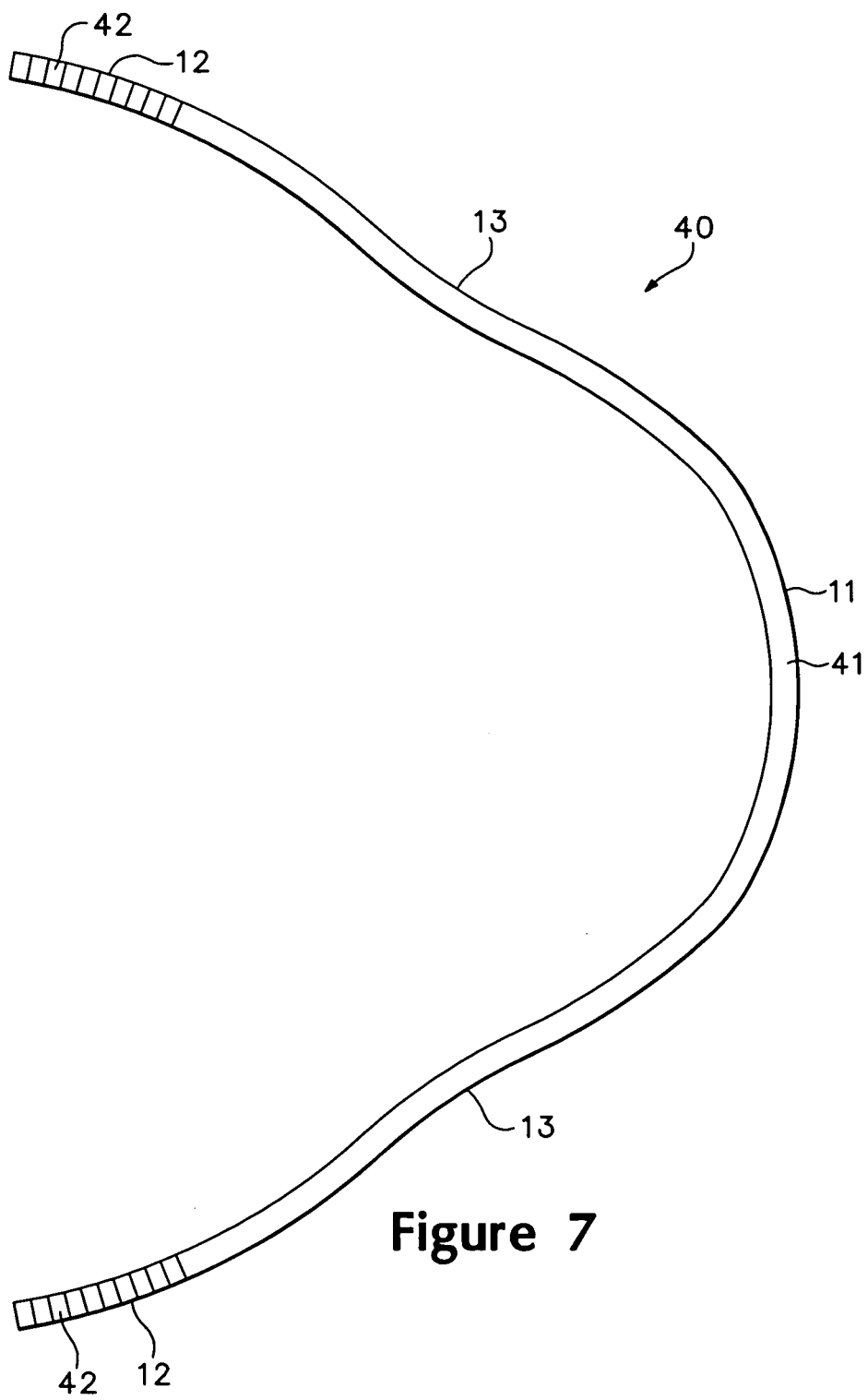
FIG. 7 is a top plan view of a peripheral support of the article of headwear in an unflexed configuration.

Support 40 is a thin and elongate member that forms a generally elliptical or otherwise looped structure extending around the periphery of headwear 10. With reference to FIG. 7, support 40 is depicted in an unflexed configuration and has a generally v-shaped structure that includes a rounded vertex. Although support 40 may merely be a straight rod that is flexed when incorporated into headwear 10, support 40 is depicted as being molded with particular contours. That is, support 40 has a rounded central portion 41, a pair of end portions 42 that extend outward from central portion 41, and a generally undulating structure between central portion 41 and end portions 42. When end portions 42 are flexed toward each other, which occurs when support 40 is incorporated into headwear 10, support 40 exhibits the generally elliptical or otherwise looped structure depicted in FIG. 8.

Figure 3:
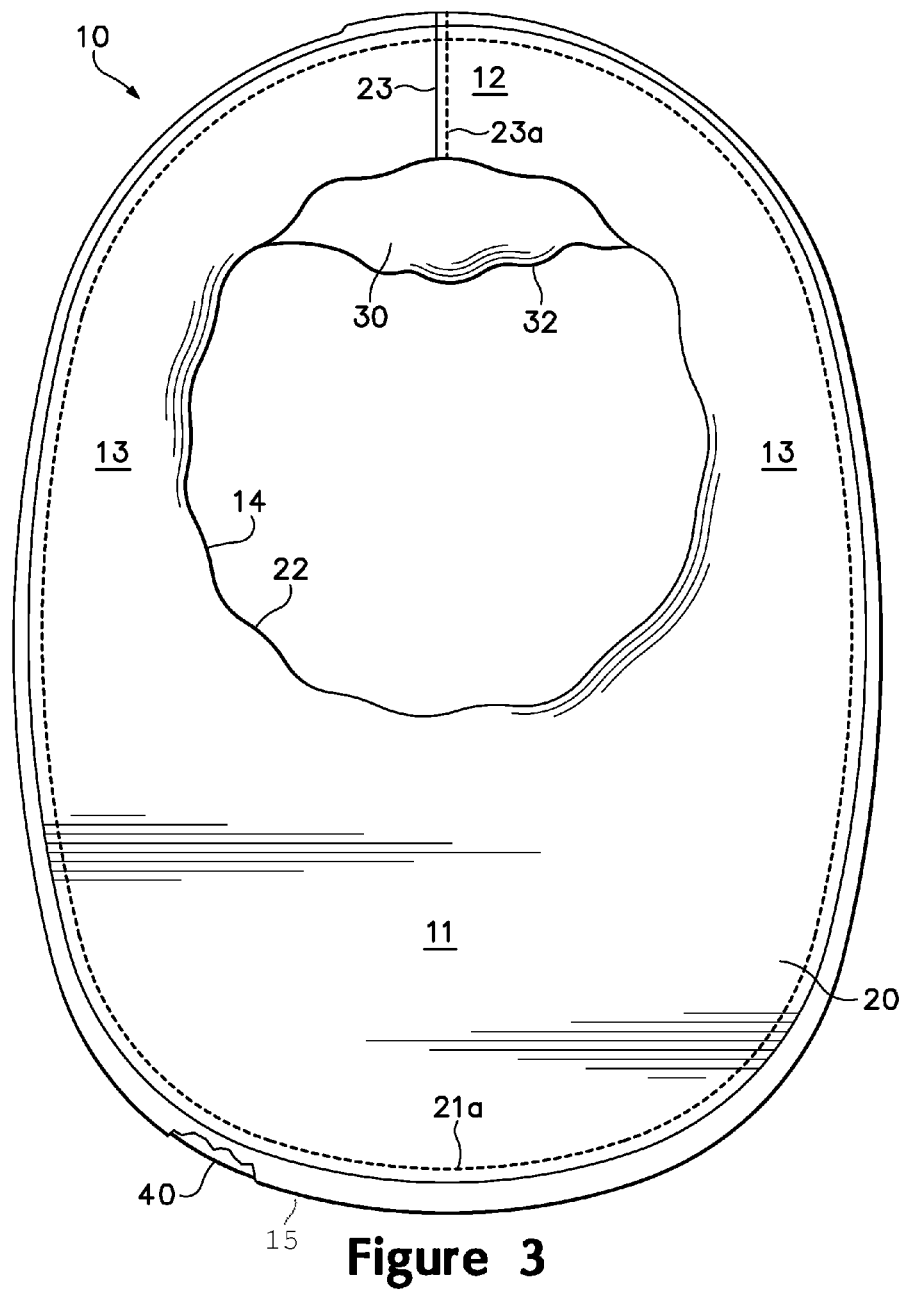
FIG. 3 is a top plan view of the article of headwear.
Figure 4:
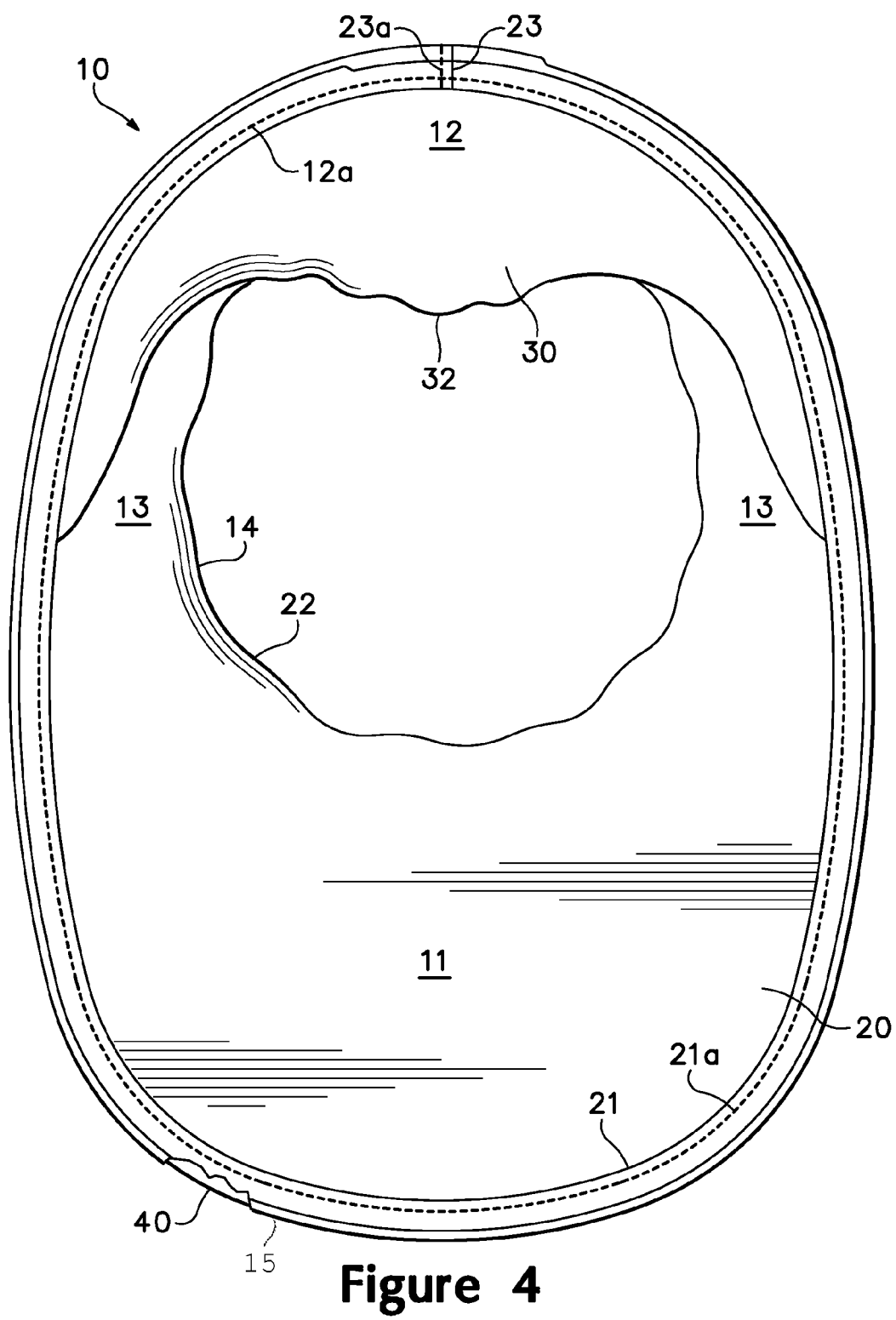
FIG. 4 is a bottom plan view of the article of headwear.

Support 40 extends through the generally tubular structure 15 formed by first material element 20 when incorporated into headwear 10. Although adhesives or various mechanical fasteners may be utilized to secure support 40 within the tubular structure 15, support 40 may also be merely located within the tubular structure 15 and restrained from significant movement by the tubular structure 15. Support 40 is flexed to conform with the shape of first material element 20 and provides an outwardly-directed force that retains the general shape of headwear 10 depicted in FIGS. 3 and 4. That is, support 40 tends to resist flexing, which places an outward force on first material element 20.

The contours of support 40 include the undulating structure between central portion 41 and end portions 42. When flexed, this undulating structure forms the downwardly-bowed configuration depicted in FIG. 2. In other words, support 40 bends downward in forward region 11 to form a brim that extends over the face of the individual. If headwear 10 is worn in the upside-down configuration, then support 40 bends upward in forward region 11.

Figure 8:
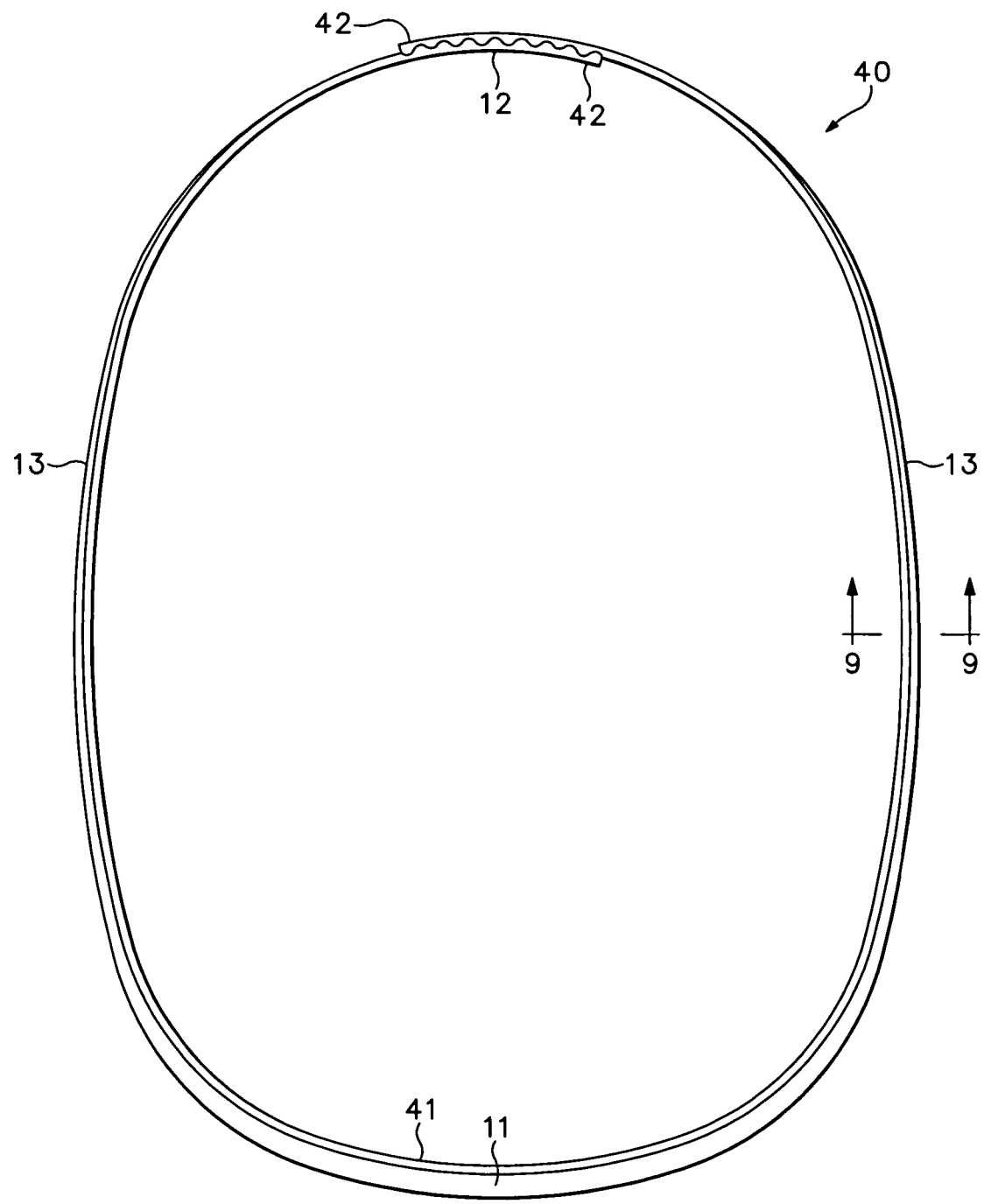
FIG. 8 is a top plan view of a peripheral support of the article of headwear in a flexed configuration.
Figure 9:
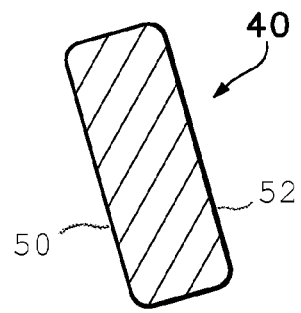
FIG. 9 is a cross-sectional view of the peripheral support, as defined along section line 9-9 in FIG. 8.
Figure 10:
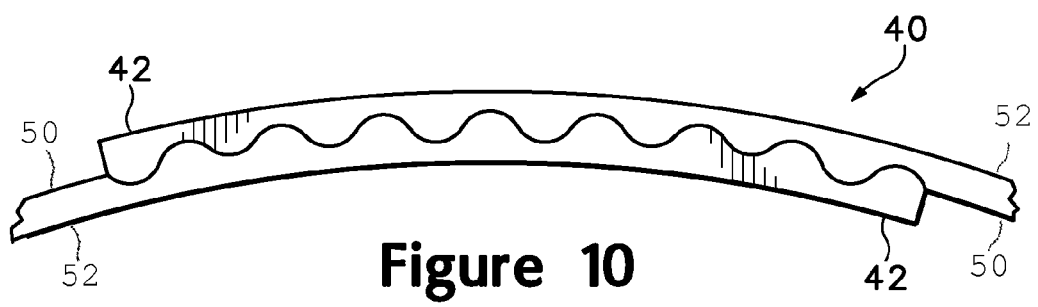
FIG. 10 is a partial plan view of end portions of the peripheral support in the flexed configuration.

Support 40 has a generally rectangular cross-sectional shape, as depicted in FIG. 9, that includes two major surfaces (i.e., the surfaces with greatest surface area), as depicted in FIGS. 9 and 10 as major surface 50 and major surface 52. As best seen in FIG. 8, the major surfaces of the cross-section approach a horizontal orientation in forward region 11. The major surfaces rotate to a diagonal orientation in side regions 13, and the major surface are substantially vertical in rearward region 12. The varying orientation of the major surfaces may be due to the manner in which support 40 is molded. The cross-sectional shape of support 40 may vary significantly from the rectangular shape depicted in the figures to include square, round, or triangular cross-sectional shapes, for example.

End portions 42 overlap each other in rearward region 12, as depicted in FIGS. 8 and 10. In order to limit the degree to which end portions 42 slide relative to each other, end portions 42 may exhibit corresponding undulating configurations. Movement of end portions 42 provides headwear 10 with adjustability for different head dimensions and shapes. The configuration of end portions 42 permits end portions 42 to move relative to each other, but limits the degree to which end portions 42 move.

An injection-molding process or compression-molding process, for example, may be utilized to form support 40 from a diverse range of materials. Suitable materials for support 40 include polyester, thermoset urethane, thermoplastic urethane, various nylon formulations (e.g., nylon 6 or nylon 11), polypropylene, or blends of these materials. In addition, support 40 may be formed from a high flex modulus polyether block amide, such as PEBAX, which is manufactured by the Atofina Company. Polyether block amide provides a variety of characteristics that may benefit the present invention, including relatively high impact resistance at low temperatures, few property variations in the temperature range of minus 40 degrees Celsius to positive 80 degrees Celsius, resistance to degradation by a variety of chemicals, and low hysteresis during alternative flexure. Another suitable material for support 40 is a polybutylene terephthalate, such as HYTREL, which is manufactured by E.I. duPont de Nemours and Company. Composite materials may also be formed by incorporating glass fibers or carbon fibers into the polymer materials discussed above in order to enhance the strength of support 40.

Figure 11:
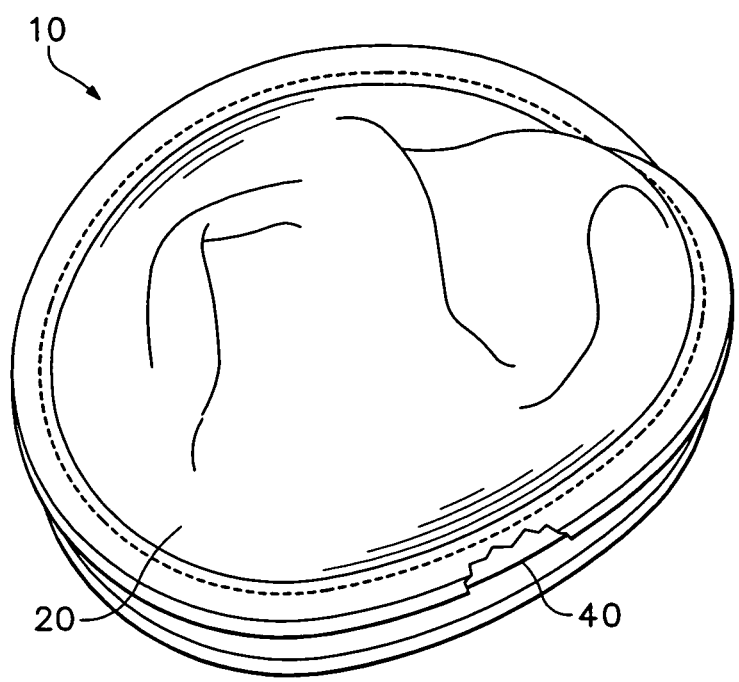
FIG. 11 is a perspective view of the article of headwear in a collapsed configuration.

The flexible configuration of support 40 permits headwear 10 to be stored in a compact manner when not worn. Referring to FIG. 11, headwear 10 is depicted in a collapsed configuration wherein support 40 generally forms three loops and material elements 20 and 30 overlap each other and are located on an interior area of the loops. In order to convert headwear 10 from the non-collapsed configuration, as in FIGS. 1-4, to the collapsed configuration, the individual twists support 40 to form the three loops. In the collapsed configuration, headwear 10 exhibits dimensions that are generally sufficient for storage in pants pockets, shirt pockets, or a purse, for example.

The present invention is disclosed above and in the accompanying drawings with reference to a variety of embodiments. The purpose served by the disclosure, however, is to provide an example of the various features and concepts related to the invention, not to limit the scope of the invention. One skilled in the relevant art will recognize that numerous variations and modifications may be made to the embodiments described above without departing from the scope of the present invention, as defined by the appended claims.

That which is claimed is:

1. An article of headwear comprising:
a molded support having an elongate structure that defines a first end portion and a second end portion, the molded support being flexed such that the first end portion is positioned adjacent the second end portion to define a loop with an interior area;
a first material element extending around the interior area of the loop to define an aperture for receiving a head of an individual, wherein an outer edge of the first material element wraps around the molded support to define a tubular structure for receiving the molded support; and
a second material element secured to the first material element and positioned adjacent the first end portion and the second end portion of the molded support, the second material element being located substantially within the interior area of the loop and the second material element extending only partially around the interior area of the loop to define a flap; wherein the first end portion and the second end portion overlap each other within the tubular structure to define an overlapped area of the molded support, and the first end portion and the second end portion have mating undulating configurations in at least a portion of the overlapped area, wherein the mating undulating configurations provide the article of headwear with adjustability for different head dimensions;

wherein the molded support has a rectangular cross-section that defines a first major surface and an opposite second major surface, wherein the rectangular cross-section of the molded support is designed to have a varying orientation that includes a horizontal orientation in a forward region, a diagonal orientation in side regions, and a vertical orientation in a rearward region.

2. The article of headwear recited in claim 1, wherein the elongate structure is a generally elliptical structure and wherein the forward region is formed from a rounded central portion of a generally v-shaped structure exhibited by the molded support when the molded support is unflexed.

3. The article of headwear recited in claim 1, wherein each of the first material element and the second material element are formed of unitary construction from elastic textiles.

4. The article of headwear recited in claim 1, wherein the first material element has a c-shaped configuration with a central area and two end areas, the end areas being joined to form the aperture.

5. The article of headwear recited in claim 4, wherein the second material element has a crescent-shaped configuration.

6. The article of headwear recited in claim 1, wherein the molded support may be flexed to form multiple loops and place the article of headwear in a collapsed configuration.

7. The article of headwear recited in claim 1, wherein the first major surface includes the mating undulating configurations of the first end portion, the second major surface includes the mating undulating configurations of the second end portion, the first major surface includes a portion, opposite the mating undulating configurations of the second major surface at the same end portion, that is without an undulating configuration.

8. The article of headwear recited in claim 1, wherein the molded support bends downward in the forward region to form a brim of the article of headwear.

9. An article of headwear comprising:
 a molded support extending around a periphery of the article of headwear and having an elongate structure that defines a first end portion and a second end portion, the molded support being flexed such that the first end portion overlaps the second end portion to define an elliptical loop with an interior area, the first end portion and the second end portion having mating undulating configurations; and
 a material element extending around the interior area of the elliptical loop to define an aperture for receiving a head of an individual, an outer edge of the material element wrapping around the molded support to define a tubular structure for receiving the molded support;
 wherein the mating undulating configurations of the first and second end portions overlap each other within the tubular structure to define an overlapped area of the molded support and provide the article of headwear with adjustability for different head dimensions, and
 wherein the molded support has a rectangular cross-section that defines a first major surface and an opposite second major surface, wherein the rectangular cross-section of the molded support is designed to have a varying orientation that includes a horizontal orientation in a forward region, a diagonal orientation in side regions, and a vertical orientation in a rearward region.

10. The article of headwear recited in claim 9, wherein the elongate structure is a generally elliptical structure, and wherein the forward region is formed from a rounded central portion of a generally v-shaped structure exhibited by the molded support when the molded support is unflexed.

11. The article of headwear recited in claim 9, wherein the molded support may be flexed to form multiple loops and place the article of headwear in a collapsed configuration.

12. The article of headwear recited in claim 9, wherein the material element has a c-shaped configuration with a central area and two end areas, the end areas being joined to form the aperture.

13. The article of headwear recited in claim 9, wherein the material element is formed of unitary construction from elastic textiles.

14. The article of headwear recited in claim 9, further including another material element located substantially within the interior area of the elliptical loop and extending only partially around the interior area of the elliptical loop.

15. The article of headwear recited in claim 9, wherein another material element with a crescent-shaped configuration is positioned adjacent the first end portion and the second end portion of the molded support.

16. The article of headwear recited in claim 9, wherein the molded support bends downward in the forward region to form a brim of the article of headwear.

17. The article of headwear recited in claim 9, wherein the first major surface includes the mating undulating configurations of the first end portion, the second major surface includes the mating undulating configurations of the second end portion, and the first major surface includes a portion opposite the mating undulating configurations of the second major surface at the same end portion without an undulating configuration.

18. An article of headwear comprising:
 a molded support having an elongate structure that defines a first end portion and a second end portion, the molded support being flexed such that the first end portion is positioned adjacent the second end portion to define a loop with an interior area, the first end portion and the second end portion overlapping each other to define an overlapped area of the molded support, and the first end portion and the second end portion having mating undulating configurations in at least a portion of the overlapped area;
 a first material element having a c-shaped configuration with a central area and two end areas, the end areas being joined to form an aperture for receiving a head of an individual, and an edge of the first material element wraps around the molded support to define a tubular structure for receiving the molded support, the first material element being formed from a textile material; and
 a second material element secured to the first material element and positioned adjacent the first end portion and the second end portion of the molded support, the second material element being located substantially within the interior area of the loop, the second material element having a crescent-shaped configuration, and the second material element extending only partially around the interior area of the loop to define a flap and wherein at least a portion of the second material element stretches across the interior area of the loop, wherein the flap is configured to assist in securing the article of headwear to the individual,
 wherein the mating undulating configurations overlap each other within the tubular structure to define an overlapped area of the molded support, wherein the mating undulating configurations provide the article of headwear with adjustability for different head dimensions, and wherein the molded support has a rectangular cross-section that defines a first major surface and an opposite second major surface, wherein the rectangular cross-section of the molded support is designed to have a varying orientation that includes a horizontal orientation in a forward region, a diagonal orientation in side regions, and a vertical orientation in a rearward region.

19. The article of headwear recited in claim 18, wherein elongate structure is a generally elliptical structure, and wherein the forward region is formed from a rounded central portion of a generally v-shaped structure exhibited by the molded support when the molded support is unflexed.

20. The article of headwear recited in claim 18, wherein each of the first material element and the second material element are formed of unitary construction from elastic textiles.

21. The article of headwear recited in claim 18, wherein the molded support is configured to be flexed to form at least two loops and place the article of headwear in a collapsed configuration.

\* \* \* \* \*